(12) United States Patent
Recto

(10) Patent No.: US 6,409,709 B1
(45) Date of Patent: Jun. 25, 2002

(54) OSTOMY-CHANGING FACILITATING DEVICE

(76) Inventor: Sylvia Recto, 46500 Maidstone, Canton, MI (US) 48187

( * ) Notice: Subject to any disclaimer, the term of this patent is extended or adjusted under 35 U.S.C. 154(b) by 0 days.

(21) Appl. No.: 09/573,972

(22) Filed: May 19, 2000

(51) Int. Cl.[7] .................................................. A61F 5/44
(52) U.S. Cl. ...................... 604/339; 604/338; 604/337; 604/339; 604/327
(58) Field of Search ................................ 604/322, 327, 604/337, 338, 339, 341, 342, 354, 355, 539

(56) References Cited

U.S. PATENT DOCUMENTS 4,187,850 A  *  2/1980  Gust ........................... 128/283
5,147,340 A  *  9/1992  Lavender .................... 604/344

* cited by examiner

*Primary Examiner*—John G. Weiss
*Assistant Examiner*—Linh Truong

(57) ABSTRACT

A ostomy-changing facilitating device for absorbing fluids from the stoma during the change of the more permanent ostomy appliance. The ostomy-changing facilitating device includes a tubular member having a length of approximately 3 to 4 inches and having a diameter adapted to effectively surround a stoma and also having an open top end, an open bottom end and a bore extending therethrough with absorbent material filling the bore of the tubular member and being of a wick-type of material so that fluids coming from the stoma is absorbed into the wick-type of material to prevent infections during the changing of a more permanent ostomy appliance.

6 Claims, 3 Drawing Sheets

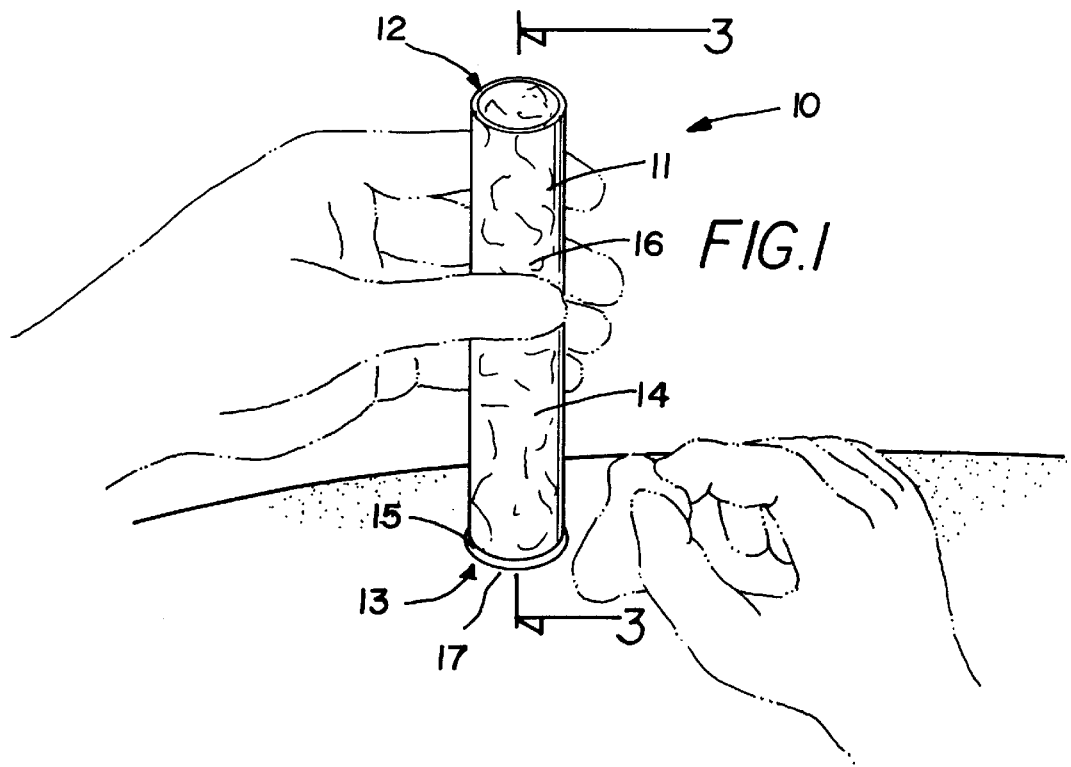
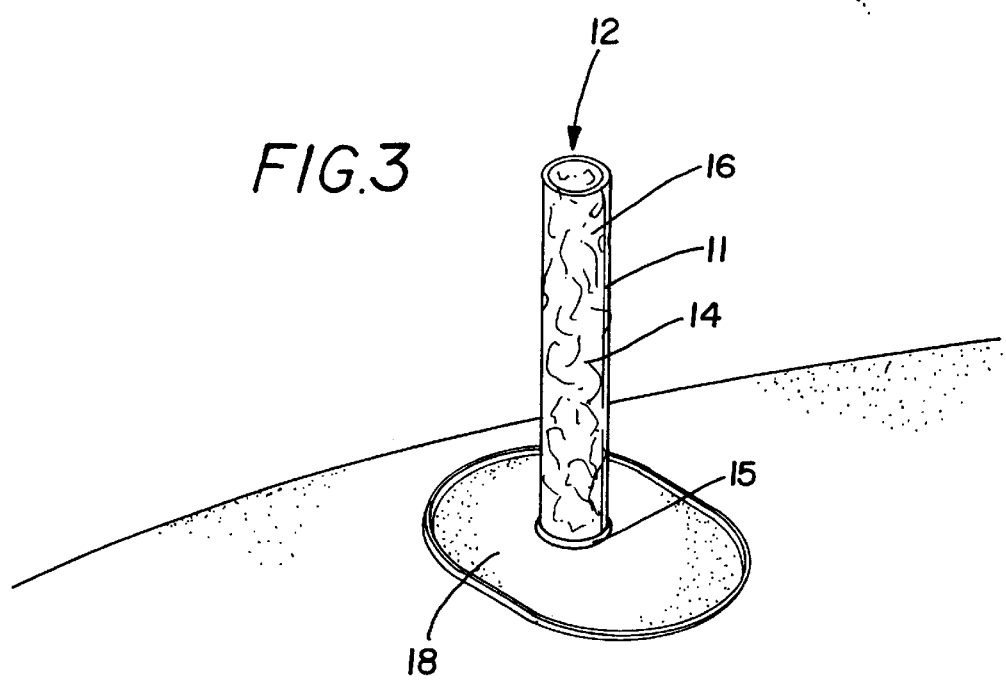

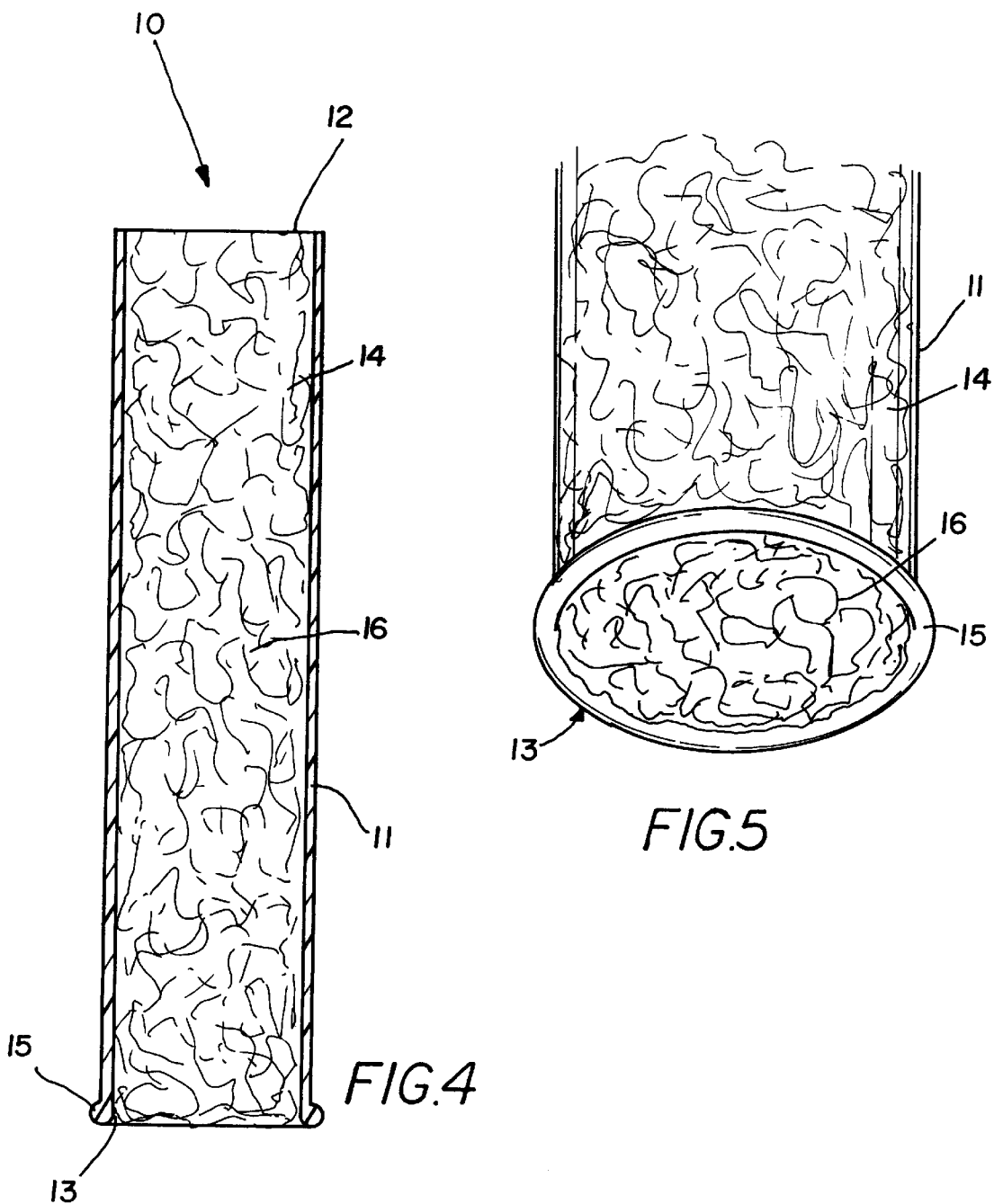

OSTOMY-CHANGING FACILITATING DEVICE

BACKGROUND OF THE INVENTION

1. Field of the Invention

The present invention relates to a two piece appliance changing device and more particularly pertains to a new ostomy-changing facilitating device for absorbing fluids from the stoma during the change of the more permanent ostomy appliance.

2. Description of the Prior Art

The use of a two piece appliance changing device is known in the prior art. More specifically, a two piece appliance changing device heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,147,340; 4,850,985; 5,167,651; 5,269,773; 4,344,433; and U.S. Pat. No. Des. 270,090.

While these devices fulfill their respective, particular objectives and requirements, the aforementioned patents do not disclose a new ostomy-changing facilitating device. The inventive device includes a tubular member having a length of approximately 3 to 4 inches and having a diameter adapted to effectively surround a stoma and also having an open top end, an open bottom end and a bore extending therethrough with absorbent material filling the bore of the tubular member and being of a wick-type of material so that fluids coming from the stoma is absorbed into the wick-type of material to prevent infections during the changing of a more permanent ostomy appliance.

In these respects, the ostomy-changing facilitating device according to the present invention substantially departs from the conventional concepts and designs of the prior art, and in so doing provides an apparatus primarily developed for the purpose of absorbing fluids from the stoma during the change of the more permanent ostomy appliance.

SUMMARY OF THE INVENTION

In view of the foregoing disadvantages inherent in the known types of two piece appliance changing device now present in the prior art, the present invention provides a new ostomy-changing facilitating device construction wherein the same can be utilized for absorbing fluids from the stoma during the change of the more permanent ostomy appliance.

The general purpose of the present invention, which will be described subsequently in greater detail, is to provide a new ostomy-changing facilitating device which has many of the advantages of the two piece appliance changing device mentioned heretofore and many novel features that result in a new ostomy-changing facilitating device which is not anticipated, rendered obvious, suggested, or even implied by any of the prior art two piece appliance changing device, either alone or in any combination thereof.

To attain this, the present invention generally comprises a tubular member having a length of approximately 3 to 4 inches and having a diameter adapted to effectively surround a stoma and also having an open top end, an open bottom end and a bore extending therethrough with absorbent material filling the bore of the tubular member and being of a wick-type of material so that fluids coming from the stoma is absorbed into the wick-type of material to prevent infections during the changing of a more permanent ostomy appliance.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new ostomy-changing facilitating device which has many of the advantages of the two piece appliance changing device mentioned heretofore and many novel features that result in a new ostomy-changing facilitating device which is not anticipated, rendered obvious, suggested, or even implied by any of the prior art two piece appliance changing device, either alone or in any combination thereof.

It is another object of the present invention to provide a new ostomy-changing facilitating device which may be easily and efficiently manufactured and marketed.

It is a further object of the present invention to provide a new ostomy-changing facilitating device which is of a durable and reliable construction.

An even further object of the present invention is to provide a new ostomy-changing facilitating device which is susceptible of a low cost of manufacture with regard to both materials and labor, and which accordingly is then susceptible of low prices of sale to the consuming public, thereby making such ostomy-changing facilitating device economically available to the buying public.

Still yet another object of the present invention is to provide a new ostomy-changing facilitating device which provides in the apparatuses and methods of the prior art some of the advantages thereof, while simultaneously overcoming some of the disadvantages normally associated therewith.

Still another object of the present invention is to provide a new ostomy-changing facilitating device for absorbing fluids from the stoma during the change of the more permanent ostomy appliance.

Yet another object of the present invention is to provide a new ostomy-changing facilitating device which includes a tubular member having a length of approximately 3 to 4 inches and having a diameter adapted to effectively surround a stoma and also having an open top end, an open bottom end and a bore extending therethrough with absorbent material filling the bore of the tubular member and being of a wick-type of material so that fluids coming from the stoma is absorbed into the wick-type of material to prevent infections during the changing of a more permanent ostomy appliance.

Still yet another object of the present invention is to provide a new ostomy-changing facilitating device that greatly prevents infection to the stoma during the change of ostomy appliances.

Even still another object of the present invention is to provide a new ostomy-changing facilitating device that adds to the comfort of the user during the changing of more permanent ostomy appliances.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new ostomy-changing facilitating device according to the present invention and being put to use.

FIG. 3 is a perspective view of the present invention.

FIG. 4 is a side elevational view of the present invention.

FIG. 5 is a detailed perspective view of the bottom end of the tubular member of the present invention.

DESCRIPTION OF THE PREFERRED EMBODIMENT

Figure 2:
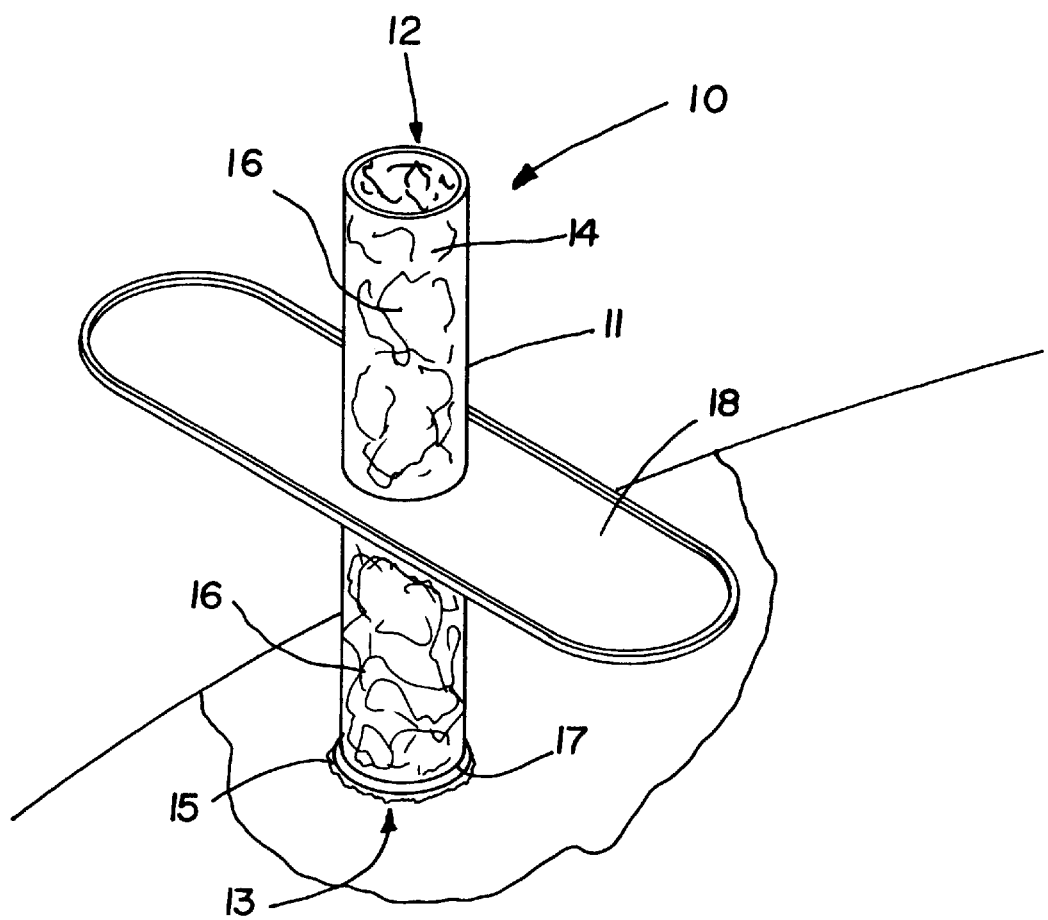
FIG. 2 is a perspective view of the present invention in use with a skin barrier member being down about the tubular member to the user's skin.

With reference now to the drawings, and in particular to FIGS. 1 through 5 thereof, a new ostomy-changing facilitating device embodying the principles and concepts of the present invention and generally designated by the reference numeral 10 will be described.

As best illustrated in FIGS. 1 through 5, the ostomy-changing facilitating device 10 generally comprises a tubular member 11 having an open top end 12, an open bottom end 13 and a bore 14 extending therethrough with the bottom end 12 being adapted to be disposed over and about a stoma 17. The tubular member 11 is essentially a cylindrical member having a rounded annular lip 15 extending along an edge of the cylindrical member at the bottom end 13 for facilitating contact with a user's skin 19 about the stoma 17. The cylindrical member 11 has a length of approximately 3 to 4 inches and has a diameter which is adapted to generally and effectively surround and seal about the stoma 17. The cylindrical member 11 is adapted to allow a skin barrier member 18 to slide down over and about the cylindrical member 11 and to adhere to a user's skin 19 around the stoma 17. An absorbent material 16 is conventionally disposed or wedged in the bore 14 of the tubular member 11 for absorbing fluids from the stoma 17. The absorbent material 16 generally fills the bore 15 of the cylindrical member 11 with the absorbent material 16 being essentially a wick-type of material which draws fluids into itself.

In use, the user swabs about the stoma 17 with a cleansing member after the permanent two piece ostomy appliance is removed from over the stoma 17, and places the bottom end 13 of the cylindrical member 11 over the stoma 17 to draw the fluids coming from the stoma 17 into the absorbent material 16 which is wedged inside the cylindrical member 11.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An ostomy-changing facilitating device comprising:
   a tubular member having an open top end, an open bottom end and a bore extending therethrough with said bottom end being adapted to be disposed over a stoma; and
   an absorbent material disposed in said bore of said tubular member for absorbing fluids from the stoma;
   wherein said tubular member comprises a substantially cylindrical member having a rounded annular lip extending along an edge of said cylindrical member at said bottom end for facilitating contact with a user's skin and sealing about the stoma.

2. An ostomy-changing facilitating device as described in claim 1, wherein said cylindrical member has a length of approximately 3 to 4 inches and has a diameter which is adapted to generally and effectively surround the stoma.

3. An ostomy-changing facilitating device as described in claim 1, wherein said absorbent material generally fills said bore of said cylindrical member.

4. An ostomy-changing facilitating device as described in claim 1, wherein said absorbent material is essentially a wick-type of material which draws fluids into itself.

5. An ostomy-changing facilitating device as described in claim 1, wherein said cylindrical member is adapted to allow a skin barrier member to slide down over and about said cylindrical member and to adhere to a user's skin around the stoma.

6. An ostomy-changing facilitating device comprising:
   a tubular member having an open top end, an open bottom end and a bore extending therethrough with said bottom end being adapted to be disposed over a stoma, said tubular member being essentially a cylindrical member having a rounded annular lip extending along an edge of said cylindrical member at said bottom end for facilitating contact with a user's skin and sealing about the stoma, said cylindrical member having a length of approximately 3 to 4 inches and having a diameter which is adapted to generally and effectively surround the stoma, said cylindrical member being adapted to allow a skin barrier member to slide down over and about said cylindrical member and to adhere to a user's skin around the stoma; and an absorbent material disposed in said bore of said tubular member for absorbing fluids from the stoma, said absorbent material generally filling said bore of said cylindrical member, said absorbent material being essentially a wick-type of material which draws fluids into itself.

* * * * *